United States Patent [19]

Tache et al.

[11] Patent Number: 5,302,897
[45] Date of Patent: Apr. 12, 1994

[54] NMR ANALYSIS OF POLYPROPYLENE IN REAL TIME

[75] Inventors: Ronald J. Tache, Malden; Ajoy Roy, Danvers; Ronald L. Dechene, Boxford, all of Mass.; Thomas B. Smith, Atkinson, N.H.; Scott A. Marino, Haverhill, Mass.

[73] Assignee: Auburn International, Inc., Danvers, Mass.

[21] Appl. No.: 885,633

[22] Filed: May 19, 1992

[51] Int. Cl.⁵ .......................................... G01R 33/20
[52] U.S. Cl. .................................... 324/307; 324/300
[58] Field of Search ............... 324/300, 307, 308, 309, 324/310, 311, 312, 313, 314, 318, 322

[56] References Cited

U.S. PATENT DOCUMENTS

5,015,954  5/1991  Dechene et al. .................... 324/307
5,049,819  9/1991  Dechene et al. .................... 324/307

*Primary Examiner*—Michael J. Tokar
*Attorney, Agent, or Firm*—Jerry Cohen; Edwin H. Paul

[57] ABSTRACT

Pulsed NMR system for industrial measurements comprising sample throughput system (P, LI, V1, V2) and user system controls (104) to establish digitized free induction decay (FID) curves (C), from which fast Gaussian, slower modified Gaussian and exponential components are determined using a Marquardt-Levenberg iteration technique, and using regression techniques to correlate the FID curve components to the physical quantities of the target nuclei.

9 Claims, 5 Drawing Sheets

NMR ANALYSIS OF POLYPROPYLENE IN REAL TIME

CROSS REFERENCE TO RELATED APPLICATIONS

This application is closely related to the U.S. Pat. No. 5,015,954 issued on 14 May 1991 to Dechene et al., and to U.S. Pat. No. 5,049,819 granted Sep. 17, 1991 to Dechene et al., both entitled "Magnetic Resonance Analysis in Real Time, Industrial Usage Mode", and U.S. Pat. application Ser. No. 07/794,931 filed Nov. 11, 1993 of Dechene et al.. Both of these patents and the patent application are of common assignment with this application, and the disclosures of all are hereby incorporated herein by reference, as though set out at length herein.

FIELD OF THE INVENTION

The present invention relates to an instrument for measurement of the type and quantity of lattice bound and free magnetically active nuclei within successive samples of a process material flow through pulsed nuclear magnetic resonance (NMR) techniques and more particularly the application of such measurement to industrial process control of moisture content, polymer content, crystallinity fraction, oil/fat fraction and other percentages of components analysis and other parameters.

BACKGROUND OF THE INVENTION

NMR techniques have grown extensively over the past forty years, most notably in the medical instrumentation areas where in vivo examination of various parts of the human body can be seen, and in clinical research laboratory uses. In addition there has been some use and interest in the application of these techniques to industrial instrumentation and control tasks. The present invention enables effective utilization (technically and economically) of pulsed NMR techniques in industrial areas to replace or complement existing optical and radiant energy-based instrumentation.

Pulsed NMR spectroscopy is described in our above-cited patents. This technique uses a burst or pulse which is designed to excite the nuclei of a particular nuclear species of a sample being measured (the protons, or the like, of such sample having first been precessed in an essentially static magnetic field); in other words the precession is modified by the pulse. After the application of the pulse there occurs a free induction decay (FID) of the magnetization associated with the excited nuclei. Traditional Fourier Transform analysis generates a frequency domain spectrum which can be used to advantage in studying the nuclei of interest. The duration of the pulses, the time between the pulses, the pulse phase angle and the composition of the sample are parameters which affect the sensitivity of this technique. These frequency domain techniques are not easily useable in industrial applications, especially on-line applications.

An object of this invention is an improved measurement system which leads to accurate, fast determination of the types and quantity of the nuclear species of interest.

A further object of this invention is its application to the industrial, on-line problems of measuring and calibrating the controlling processes per se.

Another object of this invention is to utilize time domain analysis in achieving such system.

The principal variables of interest are polymer crystallinity, tacticity and the molecular structure of polypropylene. But other parameters may be measured. It is an object of this invention to accomodate a variety of such measuring tasks.

Another object is to accommodate the dynamics of industrial on-line applications including variations of density, temperature, packing and size factors, friction and static electricity, vibrations and frequent, repetitive, cyclic and non-cyclic measurements.

A further object of the invention is to integrate all the features of accurate, fast determination of the types and quantity of the polymer molecular structure of interest, the use of time domain analysis in such a system, its application to the industrial, on-line problems of monitoring and controlling processes accommodating the dynamics of industrial on-line applications including variations of density, temperature, packing and size factors, friction and static electricity, vibration and frequent, repetitive, cyclic and non-cyclic measurements.

A further object of the invention is to use such magnetic resonance techniques in polypropylene analysis, including crystallinity, tacticity and density, all with enhanced accuracy and reliability of data obtained and while achieving the necessary practical economies.

A further object of the present invention is to extend those achievements further in relation to industrial on-line processing, and the like of NMR-active materials and wore particularly to polypropylene wherein the tacticity of the material, and the concurrent molecular structure is determined on-line.

SUMMARY OF THE INVENTION

The present invention provides a materials measurement system using magnetic resonance hardware, controls (and related data capture and data reduction means and steps) and techniques, preferably in the time domain. The system can be used to capture data from a continuous production line or like repetitive measurements system.

The NMR system effects a reliable extraction of free induction decay data in a way that is practical in an industrial on-line context and economically practical. The system is characterized by provision of a base magnetic field homogeneity to a reasonable degree and offset of inhomogeneity effects, temperature stabilization to a reasonable degree and offsets of thermal drift effects and use of multiple runs (10-50) for each measurement with digital data reduction and use of statistical methods or other data manipulation for industrially effective measurement. These data can be represented, for discussion/analysis, as a free induction decay curve (FID) with attention to time sequence components of a first, very fast Gaussian, followed by a slower modified Gaussian (a Gaussian multiplied by a cosine with an argument of $K(t)^{\frac{1}{2}}$), in turn followed by an even slower exponential. These different components are representative of proton relaxation after an initial excitation by a pulse of transmitted and near resonant coupled radio frequency energy that induces a modification of the precession of protons in the sample being measured in a high static magnetic field. The calibration system including the M-L technique (described below) will still be applicable.

The fast Gaussian FID portion is based on measurement data points of magnetization decay of a relatively immobile structure present in the polypropylene sample and picked up at the NMR system's receiver. This component can be related to the isotactic polypropylene structure. The slower modified Gaussian component is a transition zone between the constrained and the more mobile structures. The slow exponential FID portion is usually based on mobile structure. This component can be related to the atactic polypropylene structure. The fast Gaussian, the slower modified Gaussian and exponential FID portions and the FID as a whole can be extrapolated to a decay origin usually set close to the time center of the excitation pulse. Zero time intercepts of these curves provide ratio data using the FID intercept and/or intercepts of one or more of the curve portions to determine polymer tacticity or crystallinity. Density can also be determined through the invention because the FID varies predictably as a function of tacticity/crystallinity and density.

The measuring system of the invention comprises economically scaled down and industrially hardened portions, relative to the widely used laboratory systems. A magnetic essentially fixed field comprises closely spaced pole pieces with a 4,000–8,000 Gauss field (about 4,700 Gauss, nominally). Helmholtz coils are provided which are adjustable to provide rapid adjustments for the precise, correct field and overlaid with coarse, slower adjustments to thermal environment. This is to assure that the product of a materials related constant (gamma) multiplied by the magnetic field strength, which is resonant frequency, will match excitation frequency by a selected offset. Still further fine adjustment is made in signal processing as described below.

The present invention accommodates great streams of data in practical ways through features, described below, which are interrelated to the thermal controls to provide a measuring system meeting the foregoing objects. The materials of construction are also integrated into the reliability considerations, as described below. Measurement of a sample is often accomplished in approximately a minute (in contrast to hours-long measurements of many prior art systems).

The measurements made through the present invention based on ratios of intercept, delay time constants and/or integrated areas under curves and/or peak analysis are independent of weight or volume of sample in the measuring region or gain of the system whereas precise weight measurement is a necessary feature—and limitation of—many prior art systems.

Prior art efforts at industrial on-line measurement of the s&ne parameters as are treated herein have involved non-NMR gravimetric, chemical, radioactive, acoustic, optical and electrostatic/capacitive systems, none wholly satisfactory for present purpose and NM usage in support of continuous industrial processes has been a forcing of off-line laboratory instruments into service [at great expense and nevertheless with inadequate sampling] or some early efforts of the 1980's at industrially hardened pulsed NMR instruments making use of only one or two data points for FID analysis. The present invention breaks out of all those dead ends.

Laboratory methods of frequency domain NMR analysis are described for crystallinity content determination in, e.g., Spiess, "Molecular Dynamics of Solid Polymers As Revealed By Deuteron NMR", 261 Colloid & Polymer Science 193-209 (1983) and Kauffman et al., "Determination of Transition Temperatures and Crystalline Content of Linear High Molecular-Weight Polyethylene by Proton NMR Spectroscopy", 27 Jl. of Polymer Science 2203-2209 (1989). Time domain analysis using pulsed and multiple pulsed NMR free induction decay in coals for detection of free radicals therein is shown in the laboratory systems of Gerstein et al. (Iowa State University Ames Laboratory) reported in "Utility of Pulsed Nuclear Magnetic Resonance In Studying Protons In Coals", 81 Jl. of Phys. Chem. 566-571 (1977) and "1H Nuclear Magnetic Resonance Studies of Domain Structures In Polymers", 52(9) J. Appl. Phys. 5517-5528 (1981). The instruments or former instruments of IBM Federal Systems Division model and Bruker GmbH model P201 and the description in U.S. Pat. No. 4,430,719, granted Feb. 7, 1984, to Pearson are the earlier attempts referred to above as industrial use of NMR methods. The Pearson work was embodied in 1985 industrial plant control work of Kaiser Aluminum & Chemical Corp. It was not effective as a reliable quantitative device. Auburn International, Inc. offered the Pearson/Kaiser product for sale in 1987–1988 and it could not meet the needs of industrial on-line monitoring. These failures were followed by the making of the inventions of the above cited Dechene et al. patents and these as enhanced through the present invention, all solve the industrial on-line problem for various materials.

Other objects, features, and advantages will be apparent from the following detailed description of preferred embodiments taken in conjunction with the accompanying drawings in which:

DETAILED DESCRIPTION OF PREFERRED EMBODIMENTS

Figures 1, 2:
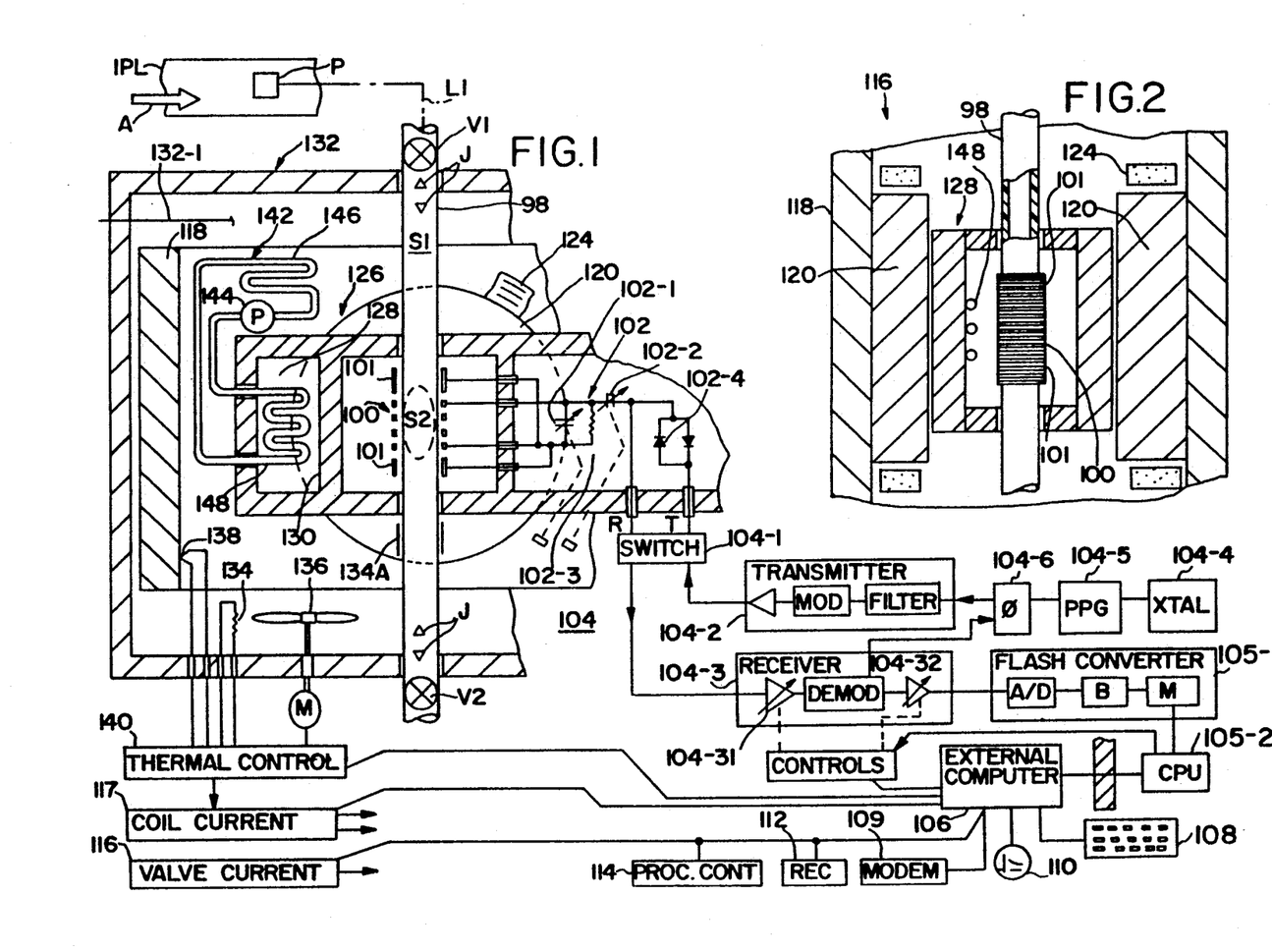
FIGS. 1 and 2 are lateral and cross-sections of a preferred embodiment of the invention including electrical block diagram components.

FIGS. 1-2 show transverse and cross sections with block diagram inserts of a first embodiment of the apparatus and method of the invention. An industrial process line IPL has material flowing as indicated by arrow A. Some of the material is captured by a probe P and fed through an inlet line LI to a sample region S1. The said region is defined by a tube 98 typically about 30 cm long made of an essentially non-magnetic, nonconducting material which does not itself generate substantially interfering FID signals (glass, certain ceramics, certain plastics or hybrids). The sample region is defined between inlet and outlet valves V1 and V2. Gas jets J are also provided. These are pulsed on/off repeatedly to agitate fluent sample materials during sample admission and expulsion. The region S2 is the critical portion of the sample. It is surrounded by a sample coil 100 tuned to resonance and driven by a tuning circuit 102 and related transmitter/receiver controller 104. Grounded loops 101 are Lenz Law shields which are provided above and below coil 100 to help shape the field of coil 100—i.e., contain the field established by an excitation pulse. The controller 104 includes an on-board microprocessor and required power supply elements, memory, program and I/O decoding suitable to interconnect to the hardware shown and to an external microcomputer 106 with keyboard 108, monitor (or other display) 110, recorder 112 and/or process controller 114 (to control the process at IPL). The operator initiates and controls operation from the display keyboard 108 and the resulting data and signals are subsequently shown on the display 100 and utilized in 110, 112 and/or 114. The computer 106 also controls instrument operation conditions.

The region S2 of tube 98 and coil 100 are in a static, but adjustable, crossing magnetic field defined by a magnetic assembly 116 which comprises a yoke 118, pole pieces 120, surrounding Helmholtz coils 124, and a coil current generator 117. The critical sample region S2 of the tube 98 and magnet are contained in a metallic (but non-ferromagnetic) box 126 with highly thermally conductive face-plates 128 and internal partitions 130 and over-all mass related to each other to minimize harmonics and other interferences with a signal emitted from coil 100 to a sample and/or returned from the sample for pick-up by coil 100 and its tuned circuit 102 and transmit/receive controller 104.

The magnetic assembly 116 including yoke 118, and other parts therein as shown on FIGS. 1-2, is in turn contained in an environmental control chamber 132 with optional inert gas fill and purge controls (not shown), an internal gas heater 134, a motor M driving fan 136, and a temperature sensor 138 which can be applied to the yoke or other detection region whose temperature is reflective of the temperature at pole pieces 120 and in the sample region therebetween. A thermal controller 140 processes temperature signals from 138 to adjust heating/circulation at 134/136 as a coarse control and to adjust current through the Helmholtz coils 124 at magnet pole pieces 120 as a sensitive and fast fine control, as well as implementing general control instructions of computer 106. Further thermal stabilization may be provided by a closed loop heat exchanger 142 having pump 144 and coils 146 attached to yoke 118 and coils 148 attached to the plates 128 of box 126. Still further thermal stabilization may be provided by directing temperature controlled air (controller not shown) inot an annular region defined by collar 134A around the sample.

The strength, consistency and constancy of the magnetic field between poles 120 in the region S2 of the sample is thus controlled by a uniform base magnetic field in the entire region S2. The Helmholtz coils 124 are energized by the coil current controller 117 to accurately trim the final magnitude of the field in which the sample is placed. This field is the vector addition of the fields due to the magnet poles 120 and the Helmholtz coils 124. The controller 117 sets the current through the Helmholtz coils 124 using current generators. The coils 124 are wound around the magnet pole pieces such that the magnetic field created by the current in the coils 124 can add to or subtract from the field created by the magnet pole pieces. The magnitude of the current through the coils 124 determines the strength of the field added to or subtracted from the field due to the magnet pole pieces (and related yoke structure) alone.

The actual determination of the current through the Helmholtz coils is accomplished by carrying out the magnetic energy and resonance techniques hereinafter described in preliminary runs and adjusting Helmholtz current until the maximum sensitive resonance is achieved. The Helmholtz current is then adjusted to offset the system from resonance by about 1-3 KHz.

The major elements of electrical controls are tuner 102, including coils 100 and 101 and variable capacitors 102-1 and 102-2, resistor 102-3 and diodes 102-4 and constructed for timing to Q of twenty to fifty to achieve coil 100 resonance, and control 104 including a transmit/receive switch 104-1, a transmitter 104-2 and receiver 104-3, a crystal oscillator 104-4, gated pulse generator (GPG) 104-5, and phase shifter 104-6. The crystal provides a nominal twenty megahertz carrier which is phase modulated or demodulated by the MOD, DEMOD elements of transmitter 104-2 and receiver 104-3. The receiver includes variable gain amplifier elements 104-31 and 104-32 for operation. The analog signals received are fed to a high speed at least 12 bit flash A/D converter 105-1 and internal (to the instrument) CPU element 105-2, which provides data to an external computer 106 which has a keyboard 108, monitor 110, modem 109, recording elements 112 and process controller elements 114, e.g., for control of valves V1, V2 via valve controls 115 and/or to coil current controls 122, all via digital-analog converters (not shown).

The analog signal FID curve is conditioned by a Bessel filter which acts as a pre-filter and an anti-aliasing filter. After digitization the signal is time smoothed by a fast Fourier transform filter program. The combination of these filters results in a relative improvement in signal to noise ratios which enhance the accuracy of the system.

Figure 3:
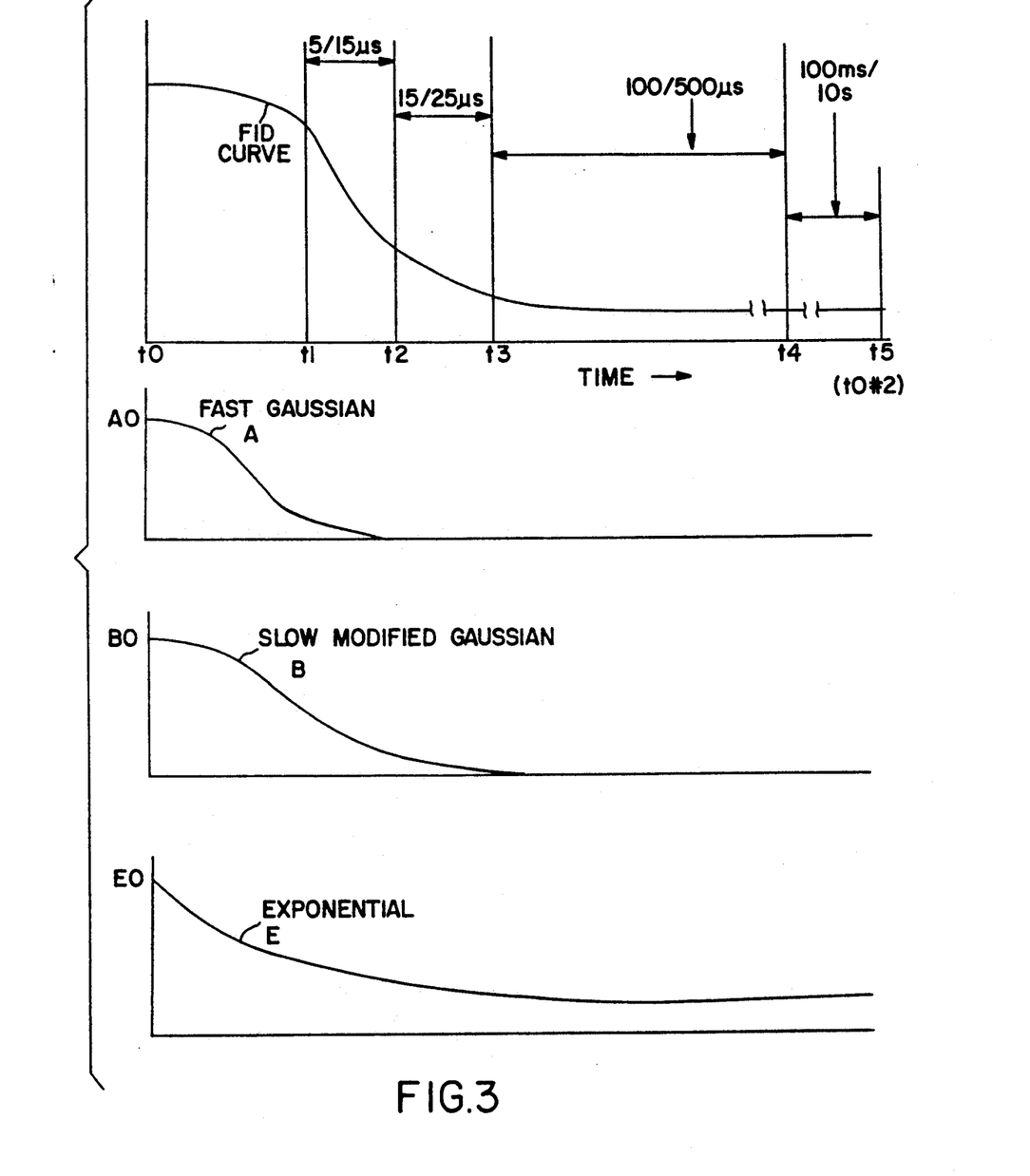
FIG. 3 shows the voltage-time waveforms of the free induction decay (FID) of the embodiment of FIGS. 1-2 in the course of operation.

The excitation of coil 100 and excitation-precession of the sample's proton content and subsequent relaxation/decay produces a received signal that, after demodulation, controlled gain amplification, A/D conversion and plotting of points has the free induction decay (FID) curve shape C shown in FIG. 3.

FIG. 3, voltage-time trace, shows the elements of a "cycle" of excitation of a sample and free induction decay. The excitation pulse center is taken as t0. The transceiver 104 electronic components do not receive effectively until saturation effects are overcome at t1. Then a useable curve is developed. The signal processing equipment can add or subtract consecutive waveforms for useful adjustment as described below.

The FID curve data are stored in the external computer 106 where a program finds the best curve to fit each stored FID curve. The FID curve has three primary component parts shown as A, B and E in FIG. 3. The A curve which dominates the first part of the FID curve is a Gaussian, while the B curve that dominates the middle part of the curve is a slower modified Gaussian, and E that dominates the later part of the FID curve is an exponential decay. The Gaussian and expoonential portions are associated with the relatively immobile and mobile portions, respectively, of the polypropylene samples. The slower modified Gaussian is a transition zone between the two. The determination of the types of curves which make up the FID curve is important because once the curves are known they can be extended back to a time origin (shown as $A_0$, $B_0$ and $E_0$ at t0, i.e., excitation of a Cycle 1), which is close to the center of the transmitted burst signal. This is important since the saturation effects of the instrument's electronic components (which occur during and after the burst signal to t1) make direct measurements of the intercepts inaccurate. The portion of the curve of interest extends from t0 to t4 beyond which the curve is too small to matter and the electronics needs recovery time to prepare for the next cycle (beginning with a pulse centered at t0#2).

Since the system is offset from resonance, the received signal is the product of the in-resonance FID and a cosine term at the offset frequency. Operation at resonance is difficult since many factors can bring the system out of resonance easily whereas operation at near resonance is relatively easily achieved and maintained. The near resonance operation of the system still yields good results since physical variations cause only minor secondary effects.

Each (sub) cycle goes on to t5 to allow for recovery i.e., essentially full relaxation of the protons of the sample before beginning a new transmit signal burst (t0#2). Typically, an excitation pulse interval is five to ten microseconds, the t0-t1 time is five to fifteen microseconds (the shorter the better), t1-t2, where effects due to the relatively immobile structure are predominant, is five to fifteen microseconds duration; t2-t3 is an transition region of fifteen to twenty-five microseconds duration, characterized by phase cancellation effects; and t3-t4 is a region of fifty to five hundred microseconds, where more mobile (exponential) structure predominates. There is a final t4-t5 region, to allow recovery (re-equilibration) of the sample material, which can be on the order of hundreds of milliseconds up to several seconds.

The entire FID curve is composed of several major components as shown in Equation Eq. 1 as applied to poypropylene and like materials, although as described there may be fewer components on some occasions. Furthermore, functions other than the fast Gaussian, slower modified Gaussian or exponential may be present in addition to or in lieu of one or more of these components, e.g. $Ce^{-(kt)}$, where lies between 0 and 1, or between 1 and 2, and these additional components can have a strong influence on the overall FID curve in early, mid or late time portions of a decay cycle.

$$F(t) = \{\cos(\Delta f)t\}\{[\text{fast Gaussian}] + [\text{slower modified Gaussian}] + [\text{exponential}]\} \quad \text{Eq. 1}$$

The entire curve is fitted by an iterative process based upon the Marquardt-Levenberg (M-L) approximation technique applied automatically through a structured implementation in software. This technique is used to determine the magnitude of all the parameters, constants, frequencies, etc. contained in Eq. 1 which best fit the FID curve—to some given error range. This is an iterative technique where the entire curve is determined at once. The M-L technique is documented in the following references: *Ind. Appl. Math.*, vol. 11, pp. 431-441 by D. W. Marquardt 1963; *Data Reduction and Error Analysis for the Physical Sciences* (New York, McGraw Hill), Chapter 11 by Philip R. Bevington 1969; and *The State of the Art in Numerical Analysis* (London: Academic Press, David A. H. Jacobs, ed 1977), chapter III.2 by J. E. Dennis. As applied to the measurement regime of interest herein in a preferred embodiment of the present invention the selected parameters are the y-axis intercept ratios and time constants, temperature coefficients, frequency terms and other parameters described below.

It was established that there are approximate limits placed upon the M-L technique which constrain the coefficients to a limited range for the types of samples described herein. If the technique is not converging after a given number of iterations, 30 in the preferred embodiment, that sample is discarded. In addition the technique may fail when the system is in resonance.

Once the equation of the FID curve is known, each component can be extrapolated back to t0 to establish the intercept of each said component.

The resulting data utilized in the computer 106 (FIGS. 1-2) is the equation for the FID curve as composed of the three (excluding the cosine term) components shown in Eq. 1. Each of these curves (and their intercepts) has been experimentally related to the same nuclei of interest. In particular, when the FID curve equation is determined, the following ratios of the y-axis intercepts of the indicated curves are formed: the exponential/fast Gaussian, (R1), and the modified Gaussian/fast Gaussian, (R2). The ratios (R1) and (R2), the cross product (R12), together with the squares of these ratios (R11) and (R22), the decay times for each of the three curve components, the product temperature and the cosine frequency term of the modified Gaussian form a ten dimensional model. A regression analysis relates these ten terms to the isotactic index (xylene solubles) of the polypropylene. The results are independent of the amount of sample, and the gain of the system, which obviates the need to measure these physical quantities.

The M-L iteration process performs the curve fitting by minimizing the Chi-Squared function (the sum of the squared differences between the measured data points and the data points from the derived equation), a technique well known in the art.

Calibration of the system is accomplished by measuring a number of known samples and using the M-L technique to derive the model equation constants associated with each known sample. Regression analysis is then performed to derive the coefficients relating the various model equation constants to the desired measured quantity or quantities. A calibration equation is then prepared using these coefficients.

In operation, a FID is obtained from the test sample and by the M-L technique the constants of the model equation are determined. These constants are then input to the calibration equation and the desired parameters are calculated.

Figure 5:
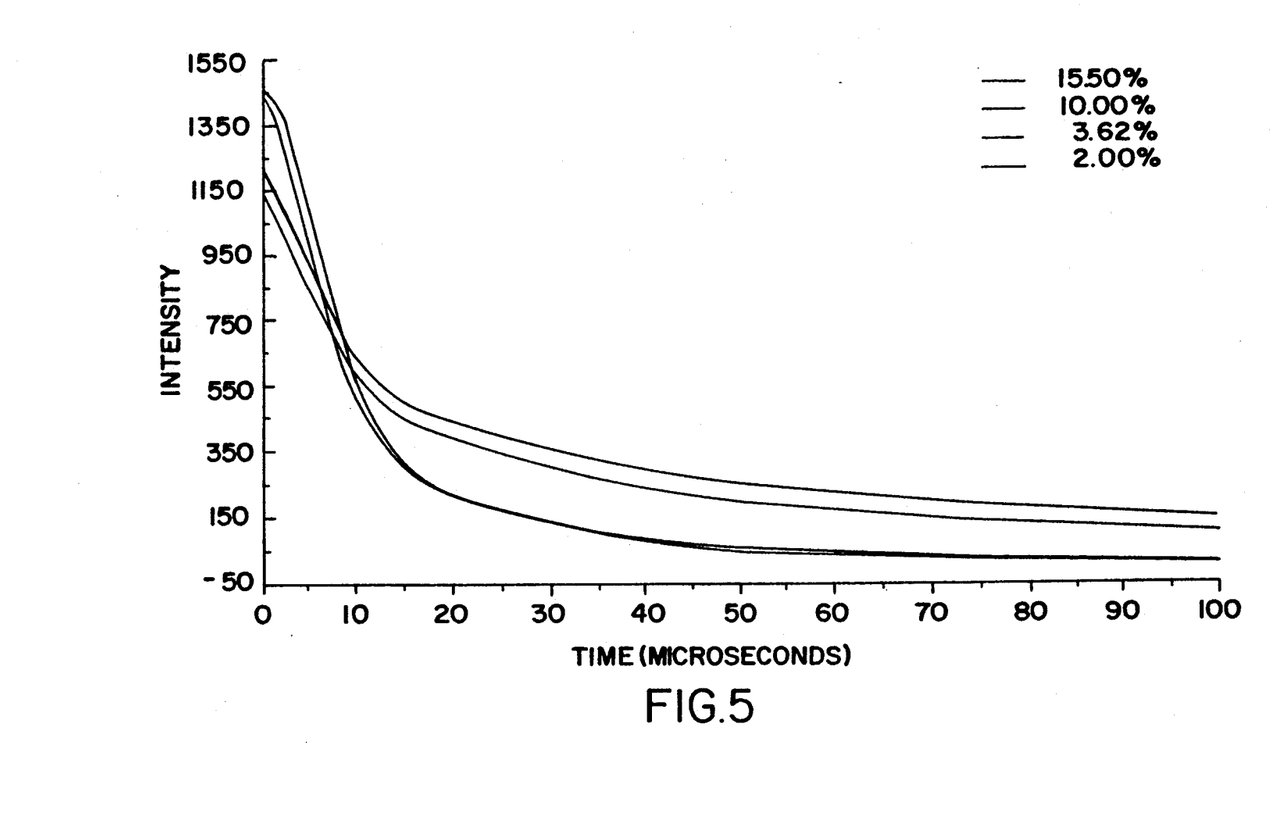
FIG. 5 is a voltage - time trace for FID curves derived from samples of polypropylene with different isotactic indices (xylene or hexane solubles)

FIG. 5 shows FID's taken for polypropylene samples of varying isotactic indices. The curves are are sufficiently distinct and the resulting three component parts found (by M-L) for each curve result, after regression, in values from which actual polypropylene isotactic index (xylene solubles) is computed from the calibration equation.

The data can be used as a QC type measurement or as an on-line control parameter which is fed back to control a process, back in line IPL (FIG. 1) or related equipment.

The form of the input operating parameters of the system can be wide reaching to include previously stored parameters in PROMs or ROMs or in magnetic storage media such as disks or tapes or inputs sent in over telephone line and modem 109. The generation of the excitation pulse can be accomplished with many techniques including a coil or antenna arrangement.

The steady magnetic field can be generated by electromagnets, permanent magnets, electromagnets with superconducting winding or other standard techniques of generating magnetic fields.

Figure 4:
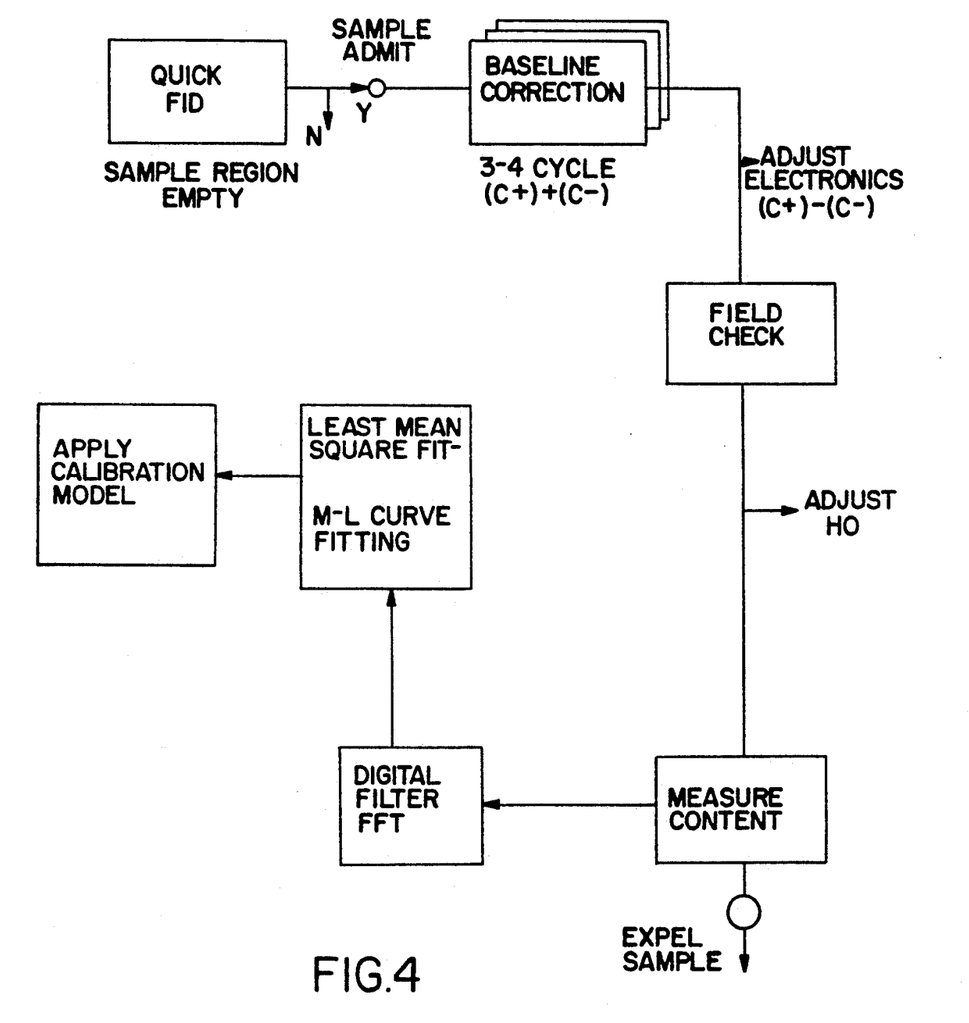
FIG. 4 is a flow chart of measuring steps utilizing the FIGS. 1-2 apparatus including its signal processing elements, (the activity of which is illustrated by the FIG. 3 waveforms)

FIG. 4 is an expanded flow chart showing the steps of measurement to establish effective industrial measurement. First a single free induction decay curve C is established to see if the sample area is clear (Quick FID) in an abbreviated cycle of attempting to establish a curve C. If the sample region is not clear (N), measurement is interrupted to allow valve V2 (re)opening and operation of jets J and gravity to clear the region. A new Quick FID step establishes clearance. Then a sample is admitted by closing valve V2, opening valve V1 and making such adjustments of probe P and line LI as may be necessary (if any) to assure sample acquisition. Jets J adjust and stabilize the new sample.

Temperature controls 134-138 and 142-146, described above, establish very coarse and less coarse thermal controls countering sample temperature variations. In addition there may be a heat guiding collar 134A that directs controlled temperature air to the sample area. Also as stated above in another preferred embodiment the heater 134 and/or the fan 136 may be disabled, thereby reducing interference, when performing high sensitivity measurements.

An electronic signal processing apparatus baseline is established in 3-4 cycles (each having (+) and (−) sub-cycles with addition of (C+) and (C−) to detect a baseline offset and compensate for it). It would be feasible to avoid this baseline offset determination and simply deal with it as an additional (i.e., eleventh) dimension in the M-L analysis, but this would increase iteration time.

Further adjustment is established by coils 124 to adjust H0 and this is enabled by ten to twenty field check cycles of FID curve generation. The (C−) FID is subtracted from the (C+) FID, i.e., the absolute C values are added to obtain a workable digitized FID signal—which has a maximum value at resonance. H0 is adjusted via coil current generator 117 and coils 124 until such maximum is achieved, and then H0 is changed to offset the system a known amount from resonance. These measurements are taken in a reliable region for such purpose, i.e., the exponential region of t3-t4 [the above baseline measurements are also taken there]. Adequate field adjustment is usually made in less than seven cycles.

Then multiple measurement cycles are usually performed to obtain useable data. Each cycle involves a modulated transmission/reception/flash A-D conversion, and storage of data. The curves are then averaged for M-L curve fitting, and the above listed intercepts and ratios are established. Similar cycles, but somewhat abbreviated can be applied for Quick FID, field check and baseline correction purposes. Each of the sub-cycles [(+) and (−)] of each such cycle involves a capture and utilization of thousands of FID points in data reduction. Each sub-cycle occurs on the order of a second and the number of such sub-cycles employed depends on the desired smoothing and signal to noise ratio (S/N); generally S/N improves in a square root relationship to the number of cycles accumulated.

As noted in above cited Dechene et al. patents, in requiring greater accuracy and reliability, sample tube composition can distort readings. If glass is not used (and it is preferred to avoid glass in industrial usage), then the replacement should not contain hydrogen. But fluorocarbons can be effective in several applications since signals from fluorine appear far from resonance. These signals can be distinguished from hydrogen at the levels of sensitivity required and if desired can be filtered (or distinguished). In other cases of higher sensitivity measurements, e.g., for gauging relative proportions of amorphous and crystalline species in mixtures thereof, the sample container should be glass or non-protonic ceramic. In some instances, however, fluorocarbon or reinforced fluorocarbon can be used acceptably for polymer measurements. In all such cases the point is to avoid sample containers with species that can couple with transmitted energy and generate a FID decay curve mimicking the samples.

Since the regression analysis involves ten variables residing in an eleven dimensional space, the results cannot be graphed. But the measurements obtained from the model represented in the present invention can be favorably compared to the results obtained from accepted off-line measuring techniques.

Figure 6:
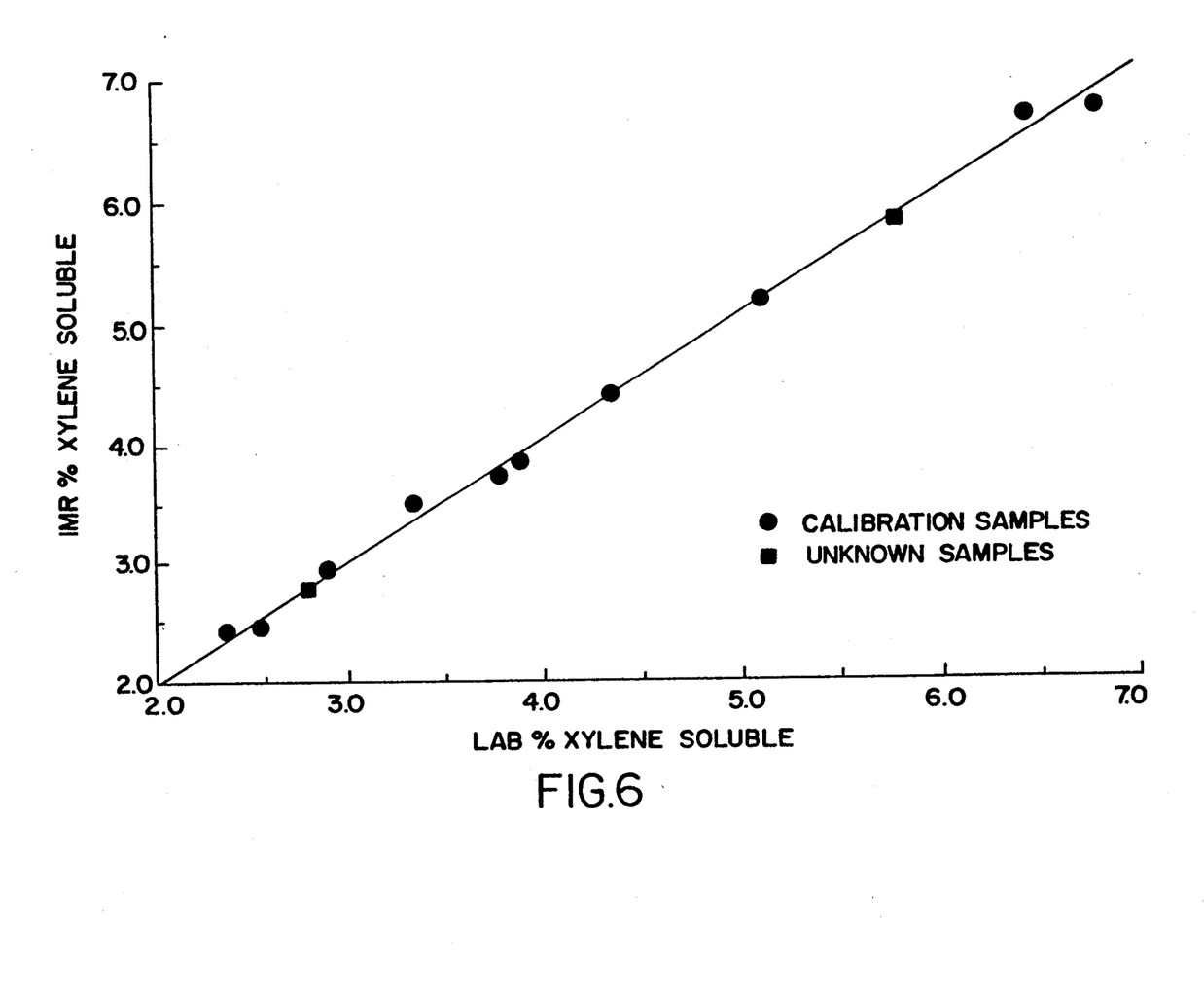
FIG. 6 is a polypropylene calibration chart.

FIG. 6 shows a calibration curve of such polypropylene xylene solubles, as measured by the present invention (y axis) vs. standard methods, illustrating the efficacy of the present invention.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. Magnetic resonance system for industrial process monitoring of polypropylene materials with unknown proportions of component nucleus structures of varying mobilities of relaxation from precession in magnetic resonance measuring processes, the system comprising:
    (a) means for accessing and removing successive samples of polypropylene from an industrial process, placing them in a sample measuring region and discarding successive samples from said region,
    (b) means for applying a base magnetic field to said region to effect precession of sample nuclei therein and applying a local excitation pulse to said region to modify the precession, wherein said excitation pulse comprises frequency characteristics offset from resonance,
    (c) means defining transmit/receive antenna coil means and signal translating means interacting with the sample to effect a precession of nuclei to be measured and relaxation detected at the coil means as a free induction decay curve,
    (d) means for establishing a digitized version of the free induction decay and making an analysis of it to components of the decay curve corresponding to true characteristics of the samples, said analysis comprising:
        establishing zero intercepts and time characteristics from said curve components
        and wherein said means (a)-(c) are constructed and arranged to effect such measurement and analysis to measure the number of decay curve regions corresponding to structures of differing mobilities of relaxation.

2. A system as defined in claim 1 wherein said means for determination of said curve components of said decay curve comprises means utilizing a Marquardt- Levenberg iteration for converting said digitized version of said free induction decay into the time equation of said decay curve and establishing said zero intercepts and time characteristics of said curve.

3. A system as defined in claim 1 wherein means for analyzing the free induction decay components corresponding to quantities of target nuclei of the samples comprises: means for establishing calibration equation wherein the zero intercepts and time constant characteristics of said decay curve components of standard samples are related to the known physical quantities of target nuclei in said standard samples, and means for calculating said physical quantities of interest by using said calibration equation, the zero intercepts, and the time characteristics of an unknown sample.

4. A system as defined in claim 3 wherein said means for comparing said calibration curves to the decay curve of an unknown sample comprises a regression analysis.

5. A system as defined in claim 1 further comprising:
feedback means to effect a constant thermal environment for said sample measuring region, wherein thermal drift components are nullified.

6. A process for substantially continuously monitoring industrial processes for polypropylene materials with unknown proportions of nuclear structures of varying mobilities of relaxation from precession in magnetic resonance measuring processes and utilizing magnetic resonance comprising the steps of:
accessing and removing successive samples of polypropylene from said industrial process,
placing said samples in a sample measuring region,
applying a base magnetic field to said region to effect precession of sample nuclei therein,
applying a local resonant excitation pulse to said region to modify the precession,
receiving and translating the free induction decay curve signal from the relaxation of the sample nuclei,
digitizing the free induction decay curve and analyzing it to components of the decay curve corresponding to quantities of target nuclei in the samples, said analyzing comprising:
determining the time equation of said decay curve,
establishing zero intercepts and time constant characteristics from said curve components,
relating said zero intercept and time constant characteristics to the quantity of decay curve regions corresponding to structures of differing mobilities, and discarding said sample from said region.

7. A process as defined in claim 6 wherein the determination of the time equation of the digitized decay curve comprises:
applying a Marquardt-Levenberg iteration technique to the digitized decay curve wherein said digitized curve is separated into a fast Gaussian, a slower modified Gaussian and an exponential component.

8. A process as defined in claim 6 wherein relating the zero intercepts and the time characteristics to the quantity of target nuclei of the samples comprises:
generating calibration equations relating the zero intercepts and time characteristics of the decay curve components of standard samples to known quantities of target nuclei in said standard samples, and
calculating said quantities of interest by using said zero intercepts and time characteristics measured from an unknown sample in conjunction with said calibration equation wherein said quantities of interest contained in said unknown sample are determined.

9. A process as defined in claim 8 wherein said calculating using said calibration equation and said decay curve of an unknown sample comprises a regression analysis.

* * * * *